United States Patent
Chen et al.

(10) Patent No.: US 6,206,865 B1
(45) Date of Patent: Mar. 27, 2001

(54) ABSORBENT ARTICLE HAVING A CELLULOSIC TRANSFER LAYER

(75) Inventors: Fung-jou Chen, Appleton; Rebecca Lyn Dilnik, Neenah, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 264 days.

(21) Appl. No.: 08/716,875

(22) Filed: Oct. 1, 1996

Related U.S. Application Data

(60) Provisional application No. 60/006,647, filed on Nov. 13, 1995.

(51) Int. Cl.[7] .................................................. A61F 13/15

(52) U.S. Cl. ................................................. 604/385.01

(58) Field of Search .................................. 604/373, 379, 604/380, 381, 382, 383, 384, 385.1, 374

(56) References Cited

U.S. PATENT DOCUMENTS

| | | | |
|---|---|---|---|
| 1,863,333 | 6/1932 | Heitmeyer . | |
| 1,910,872 | 5/1933 | Williams . | |
| 2,047,054 | 7/1936 | Beyer, Jr. | 128/290 |
| 2,295,016 | 9/1942 | Scribner | 128/290 |
| 2,295,439 | 9/1942 | Voigtman | 128/284 |
| 2,468,876 | 5/1949 | Hermanson | 128/290 |
| 2,564,689 | 5/1951 | Harwood et al. | 128/290 |
| 2,582,344 | 1/1952 | Milton | 128/290 |
| 2,772,678 | 12/1956 | Leupold | 128/290 |
| 2,787,271 | 4/1957 | Clark | 128/290 |
| 2,833,283 | 5/1958 | Spahr et al. | 128/290 |
| 2,900,980 | 8/1959 | Harwood | 128/290 |
| 2,960,089 | 11/1960 | Harwood et al. | 128/290 |
| 3,067,747 | 12/1962 | Wolterding et al. | 128/296 |
| 3,073,308 | 1/1963 | Stamberger | 128/287 |
| 3,088,463 | 5/1963 | Harmon | 128/290 |
| 3,143,113 | 8/1964 | Mills | 128/290 |
| 3,343,543 | 9/1967 | Glassman | 128/290 |
| 3,344,789 | 10/1967 | Arnold et al. | 128/290 |
| 3,375,827 | 4/1968 | Bletzinger et al. | 128/290 |
| 3,397,697 | 8/1968 | Rickard | 128/288 |
| 3,403,681 | 10/1968 | Hoey et al. | 128/290 |
| 3,441,023 | 4/1969 | Rijssenbeek | 128/287 |
| 3,463,154 | 8/1969 | Hendricks | 128/287 |
| 3,477,433 | 11/1969 | Dillon | 128/290 |
| 3,525,337 | 8/1970 | Simons et al. | 128/290 |
| 3,545,442 | 12/1970 | Wicker et al. | 128/296 |
| 3,589,956 | 6/1971 | Kranz et al. | 156/62.4 |
| 3,593,717 | 7/1971 | Jones, Sr. | 128/290 |

(List continued on next page.)

FOREIGN PATENT DOCUMENTS

| | | |
|---|---|---|
| 0 234 164 B1 | 9/1987 | (EP) . |
| 0 272 683 A2 | 6/1988 | (EP) . |
| 1 333 081 | 10/1973 | (GB) . |
| 2 124 907 | 2/1984 | (GB) . |
| 2 165 757 | 4/1986 | (GB) . |
| 2 180 162 | 3/1987 | (GB) . |
| 2 258 403 | 2/1993 | (GB) . |
| 2 258 840 | 2/1993 | (GB) . |
| 1-122727 U | 8/1989 | (JP) . |
| 2-168950 | 6/1990 | (JP) . |
| WO 91/00719 | 1/1991 | (WO) . |
| WO 91/11163 | 8/1991 | (WO) . |

*Primary Examiner*—Dennis Ruhl
(74) *Attorney, Agent, or Firm*—Mark L. Davis; Jerry F. Janssen; Michael L. Winkelman

(57) ABSTRACT

An absorbent article having a transfer layer is disclosed. The transfer layer is positioned between the cover and absorbent and has a mean free path ranging from about 50 microns to about 200 microns. In a preferred embodiment the transfer layer is composed of substantially a cellulosic material. Advantageously, the transfer layer is effective in distributing both the fluid-like and viscous constituents of body fluids such as menses permitting greater utilization of the absorbent capacity of the absorbent article.

20 Claims, 1 Drawing Sheet

U.S. PATENT DOCUMENTS

| | | | |
|---|---|---|---|
| 3,654,060 | 4/1972 | Goldman | 161/112 |
| 3,654,929 | 4/1972 | Nilsson et al. | 128/287 |
| 3,667,468 | 6/1972 | Nystrand et al. | 128/290 |
| 3,699,966 | 10/1972 | Chapuis | 128/290 R |
| 3,746,592 | 7/1973 | Nystrand et al. | 156/202 |
| 3,749,627 | 7/1973 | Jones, Sr. | 156/268 |
| 3,759,262 | 9/1973 | Jones, Sr. | 128/290 R |
| 3,771,525 | 11/1973 | Chapuis | 128/290 R |
| 3,865,112 | 2/1975 | Roeder | 128/290 R |
| 3,886,941 | 6/1975 | Duane et al. | 128/287 |
| 3,929,135 | 12/1975 | Thompson | 128/287 |
| 3,932,322 | 1/1976 | Duchane | 260/17.4 GC |
| 3,939,838 | 2/1976 | Fujinami et al. | 128/290 R |
| 3,945,386 | 3/1976 | Anczurowski et al. | 128/287 |
| 3,954,107 | 5/1976 | Chesky et al. | 128/290 R |
| 3,965,906 | 6/1976 | Karami | 128/287 |
| 3,967,623 | 7/1976 | Butterworth et al. | 128/287 |
| 3,994,299 | 11/1976 | Karami | 128/287 |
| 4,014,341 | 3/1977 | Karami | 128/287 |
| 4,029,101 | 6/1977 | Chesky et al. | 128/290 R |
| 4,037,602 | 7/1977 | Hawthorne | 128/287 |
| 4,057,061 | 11/1977 | Ishikawa et al. | 128/284 |
| 4,069,822 | 1/1978 | Buell | 128/294 |
| 4,079,739 | 3/1978 | Whitehead | 128/290 R |
| 4,100,324 | 7/1978 | Anderson et al. | 428/288 |
| 4,195,634 | 4/1980 | DiSalvo et al. | 128/290 R |
| 4,223,677 | 9/1980 | Anderson | 128/287 |
| 4,232,674 | 11/1980 | Melican | 128/287 |
| 4,276,338 | 6/1981 | Ludwa et al. | 428/137 |
| 4,285,343 | 8/1981 | McNair | 128/287 |
| 4,315,507 | 2/1982 | Whitehead et al. | 128/287 |
| 4,323,068 | 4/1982 | Aziz | 128/287 |
| 4,323,069 | 4/1982 | Ahr et al. | 128/287 |
| 4,324,246 | 4/1982 | Mullane et al. | 128/287 |
| 4,327,731 | 5/1982 | Powell | 128/287 |
| 4,357,939 | 11/1982 | Jackson et al. | 128/290 R |
| 4,372,312 | 2/1983 | Fendler et al. | 128/290 R |
| 4,397,644 | 8/1983 | Matthews et al. | 604/378 |
| 4,411,660 | 10/1983 | Dawn et al. | 604/396 |
| 4,433,972 | 2/1984 | Malfitano | 604/385 |
| 4,507,121 | 3/1985 | Leung | 604/361 |
| 4,531,945 | 7/1985 | Allison | 604/378 |
| 4,540,414 | 9/1985 | Wishman | 604/378 |
| 4,551,142 | 11/1985 | Kopolow | 604/378 |
| 4,589,876 | 5/1986 | Van Tilburg | 604/385 R |
| 4,608,047 | 8/1986 | Mattingly | 604/387 |
| 4,623,340 | 11/1986 | Luceri | 604/385 R |
| 4,626,254 | 12/1986 | Widlund et al. | 604/383 |
| 4,627,848 | 12/1986 | Lassen et al. | 604/370 |
| 4,629,643 | 12/1986 | Curro et al. | 428/131 |
| 4,631,062 | 12/1986 | Lassen et al. | 604/385 R |
| 4,636,209 | 1/1987 | Lassen | 604/378 |
| 4,676,786 | 6/1987 | Nishino | 604/378 |
| 4,687,478 | 8/1987 | Van Tilburg | 604/387 |
| 4,690,679 | 9/1987 | Mattingly, III et al. | 604/383 |
| 4,705,513 | 11/1987 | Sheldon et al. | 604/361 |
| 4,710,186 | 12/1987 | DeRossett et al. | 604/383 |
| 4,731,071 | 3/1988 | Pigneul | 604/385 R |
| 4,738,674 | 4/1988 | Todd et al. | 604/361 |
| 4,741,941 | 5/1988 | Englebert et al. | 428/71 |
| 4,755,413 | 7/1988 | Morris | 428/138 |
| 4,773,905 | 9/1988 | Molee et al. | 604/378 |
| 4,781,962 | 11/1988 | Zamarripa et al. | 428/138 |
| 4,798,601 | 1/1989 | Shirose et al. | 604/368 |
| 4,798,603 | 1/1989 | Meyer et al. | 604/378 |
| 4,798,604 | 1/1989 | Carter | 604/383 |
| 4,806,411 | 2/1989 | Mattingly, III et al. | 428/139 |
| 4,822,668 | 4/1989 | Tanaka et al. | 428/283 |
| 4,846,813 | 7/1989 | Raley | 604/385.1 |
| 4,846,824 | 7/1989 | Lassen et al. | 604/385.1 |
| 4,880,419 | 11/1989 | Ness | 604/368 |
| 4,886,632 | 12/1989 | Van Iten et al. | 264/156 |
| 4,892,534 | 1/1990 | Datta et al. | 604/370 |
| 4,895,749 | 1/1990 | Rose | 428/132 |
| 4,908,026 | 3/1990 | Sukiennik et al. | 604/378 |
| 4,950,264 | 8/1990 | Osborn, III | 604/385.1 |
| 4,963,139 | 10/1990 | Dabroski | 604/378 |
| 4,973,325 | 11/1990 | Sherrod et al. | 604/368 |
| 4,988,344 | 1/1991 | Reising et al. | 604/368 |
| 4,988,345 | 1/1991 | Reising | 604/368 |
| 5,009,653 | 4/1991 | Osborn, III | 604/385.1 |
| 5,013,309 | 5/1991 | Baigas, Jr. et al. | 604/368 |
| 5,037,409 | 8/1991 | Chen et al. | 604/358 |
| 5,037,412 | 8/1991 | Tanzer et al. | 604/359 |
| 5,048,589 | 9/1991 | Cook et al. | 162/109 |
| 5,125,918 | 6/1992 | Seidy | 604/386 |
| 5,135,521 | 8/1992 | Luceri et al. | 604/383 |
| 5,188,625 | 2/1993 | Van Iten et al. | 604/383 |
| 5,201,727 | 4/1993 | Nakanishi et al. | 604/390 |
| 5,219,341 | 6/1993 | Serbiak et al. | 604/631 |
| 5,248,309 | 9/1993 | Serbiak et al. | 604/368 |
| 5,257,982 | 11/1993 | Cohen et al. | 604/378 |
| 5,300,055 | 4/1994 | Buell | 604/385.1 |
| 5,368,926 | 11/1994 | Thompson et al. | 428/284 |
| 5,370,764 | 12/1994 | Alikhan | 156/553 |
| 5,374,260 * | 12/1994 | Lemay et al. | 604/378 |
| 5,382,400 | 1/1995 | Pike et al. | 264/168 |
| 5,399,412 | 3/1995 | Sudall et al. | 428/153 |
| 5,415,640 | 5/1995 | Kirby et al. | 604/383 |
| 5,466,232 * | 11/1995 | Cadieux et al. | 604/378 |

\* cited by examiner

ABSORBENT ARTICLE HAVING A CELLULOSIC TRANSFER LAYER

This application claims priority from U.S. Provisional application Ser. No. 60/006,647 filed on Nov. 13, 1995.

BACKGROUND OF THE INVENTION

The present invention relates to disposable absorbent articles having a cellulosic transfer layer positioned adjacent to a primary absorbent. More particularly, the invention relates to a cellulosic transfer layer having particular characteristics which is positioned adjacent to and overlies a portion of the bodyfacing surface of the primary absorbent Generally, disposable absorbent articles include, in their construction, an absorbent core positioned between a liquid-permeable cover and a liquid-impermeable baffle. The cover material is generally designed to allow body exudates to permeate through the cover so that the absorbent core can absorb the fluids. The baffle material is generally fluid impermeable and is positioned so that it is away from the body. As used herein, the term "absorbent articles" refers to products such as diapers, sanitary napkins, training pants, incontinent garments, overnight pads, panty liners, underarm shields, as well as other absorbent devices used for medical purposes such as surgical absorbents. Such articles are designed to absorb body fluids, such as urine, menses, blood, perspiration and other excrement discharged by the body. For purposes of clarity and illustration only, the embodiments described herein will be in the form of a sanitary napkin, also referred to as a catamenial pad, a feminine pad, an overnight pad, a panty liner, and a panty shield; all of which are designed to be worn by a woman to absorb menses and other body fluids discharged before, during, and after a menstrual period. Such products are external devices which typically are held in position by a garment adhesive or by mechanical attachment to an adjacent undergarment.

One continuing problem of disposable absorbent articles is that the bodily excretions are usually directed at one portion of the absorbent, whereas the absorptive capacity is spread over a greater area. This localized insulting of body fluid may cause a conventional sanitary napkin made of multiple layers of cellulosic material to collapse inward. This collapse prevents fluid from being conducted downward and substantially diminishes the inherent resiliency of the cellulosic material which in turn may lead to failure of the sanitary napkin and soiling of the wearer and/or her clothes.

To increase the absorbent utilization one or more transfer layers have been employed. Typically, the materials used in such transfer layers are nonwoven, polymeric webs. A disadvantage of these structures is their inherent hydrophobic nature. To increase the hydrophilicity, the web can be coated with a surfactant and constructed having a relatively dose pore structure. One example of this type of material is a meltblown material available from Kimberly-Clark Corporation.

Since menses is not a uniform composition and contains fluids, such as plasma and blood cells, and highly viscous materials such as mucus and tissue, a problem experienced by these polymeric transfer layers is that dose pore structure filters out the more fluid-like constituents. The more viscous materials, e.g. the mucus and tissue, hang on the bodyfacing surface of the transfer layer. This too may contribute to failure of the absorbent article resulting in soiling the wearer and/or her clothing. Alternative, when the transfer layer pore structure is large, insulting fluids are not sufficiently distributed allowing localized absorption of the body fluids and the problem associated with localized absorbent utilization discussed above occurs. Accordingly, there is a need for a transfer layer that can distribute both the fluid-like and the more viscous materials.

SUMMARY OF THE INVENTION

Briefly, the present invention provides a disposable absorbent article having an absorbent with a bodyfacing surface and a cellulosic transfer layer. The transfer layer is superposed over at least a portion of the bodyfacing surface and is in liquid communication with the absorbent The transfer layer has a mean free path (MFP) within the range of 50 microns to about 200 microns. In a preferred embodiment the transfer layer can have, in addition to the mean free path, one or more of the following: a mean pore size (MPS) ranging from about 18 microns to about 60 microns and an absorbency of bovine blood of less than about 20 seconds. Surprisingly, it has been discovered that a transfer layer having a mean free path within the range of about 50 microns to about 200 microns will effectively transfer both the fluid-like and viscous constituents of body fluids, such as menses, to the absorbent.

The general object of the invention is to provide an absorbent article with a cellulosic transfer layer. A more specific object of the invention is to provide a cellulosic transfer layer that will more effectively wick the more viscous constituents of body fluids, such as menses.

It is another object of the invention to provide a sanitary napkin having a cellulosic transfer layer that permits greater utilization of the absorbent capacity of the sanitary napkin.

BRIEF DESCRIPTION OF THE DRAWING

The invention will be more fully understood and further advantages of the invention will become apparent when reference is made to the following detailed description of the invention and the following drawing which is a cut-away perspective view of a sanitary napkin of the invention.

DETAILED DESCRIPTION OF THE INVENTION

Figure 1:
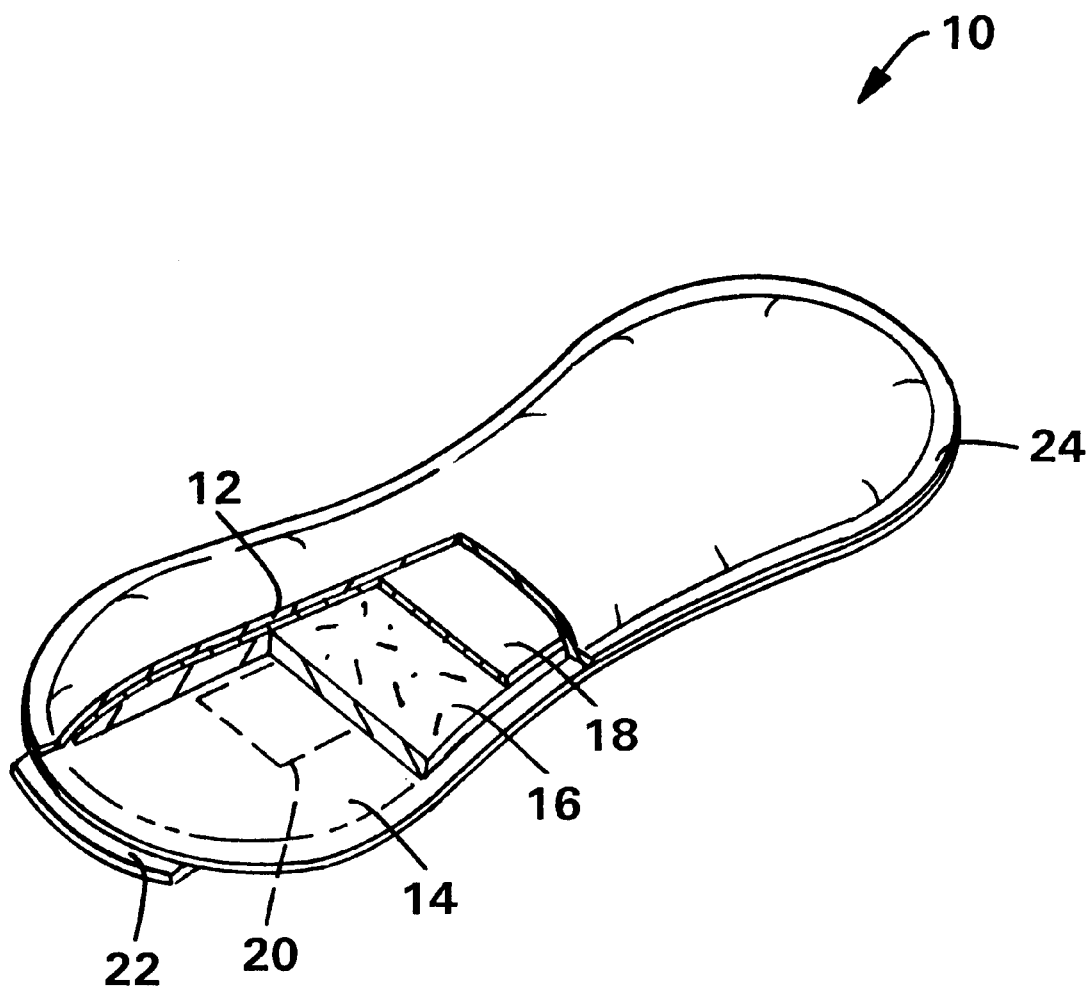

The following detailed description is made with reference to a disposable sanitary napkin article. However, it is to be understood that the absorbent structure of the present invention would also be suitable for other absorbent articles, such as diapers, adult incontinence garments, wound dressings and the like.

Referring the to the FIGURE, a sanitary napkin 10 is shown. The form and construction of the sanitary napkin 10 is generally conventional and will be described only briefly. The sanitary napkin 10 includes a bodyfacing cover 12, a garment facing baffle 14, an absorbent 16 between the cover 12 and the baffle 14 and a transfer layer 18 between the absorbent 16 and the cover 12. To secure the sanitary napkin 10 to a wearer's undergarment the sanitary napkin 10 can include a garment adhesive 20 positioned on the garment facing surface of the baffle 14. The garment adhesive 20 may also be covered by a peel strip 22 of suitable material such as silicone coated Kraft paper or a film.

Looking at the components in greater detail, the cover 12 is fluid pervious and is adapted to reside on bodyfacing side, i.e. that side of the sanitary napkin 10 in contact with the wearer's body. The cover 12 is provided for comfort and conformability and functions to direct body fluid away from the body and toward the absorbent 16. Preferably, the cover 12 is made of a material which allows the passage of fluid without wicking it appreciably in a horizontal plane parallel to the cover 12. The cover 12 should retain little or no fluid in its structure so that it provides a relatively dry surface next to the wearer's skin. The cover 12 can be constructed of any woven or nonwoven material which is easily penetrated by body fluid contacting its surface. Suitable materials include bonded carded webs of polyester, polypropylene, polyethylene, nylon, or other heat-bondable fibers, polyolefins, such as copolymers of polypropylene and polyethylene, liner low-density polyethylene, finely perforated film webs and net material also work well. Other suitable materials are composite materials of a polymer and a nonwoven fabric material. The composite sheets are generally formed by extrusion of a polymer onto a web of spunbond material to form an integral sheet. The liquid-permeable cover 12 can also contain a plurality of apertures (not shown) formed therein which are intended to increase the rate at which body fluids can penetrate down into the absorbent 16.

The cover 12 can have at least a portion of the bodyfacing surface treated with a surfactant to render the cover 12 more hydrophilic. This results in permitting the insulting liquid to more readily penetrate the cover 12. The surfactant also diminishes the likelihood that the insulting fluid, such as menstrual fluids, will flow off the cover 12 rather than being absorbed by the absorbent core 18. It is preferred that the surfactant be substantially evenly and completely distributed across at least the portion of the bodyfacing surface of the cover 12 that overlays the absorbent 16 of the sanitary napkin 10.

The absorbent 16 is generally composed of one or more materials that are hydrophilic, compressible, conformable and non-irritating to the wearers skin. Acceptable materials are known in the art and include, for example, various natural or synthetic fibers, wood pulp fibers, regenerated cellulose or cotton fibers, or a blend of pulp and other fibers. The absorbent layers may also be comprised of other known materials used in absorbent articles such as cellulose sponge, hydrophilic synthetic sponge, such as polyurethane, and the like. The total absorbent capacity of the absorbent 16 should be compatible with the design exudate loading for the intended use of the sanitary napkin 10.

The absorbent 16 can contain superabsorbent materials which are effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids. Superabsorbents can be incorporated into the absorbent 16 as separate layers or admixed with the cellulose fluff. Superabsorbents may be in the form of flakes, granules, films, particles, fibers or the like.

The baffle 14 resides on the undergarment-facing surface of the absorbent 16 and may be constructed from any desired material that is liquid-impermeable. Preferably, the baffle 14 will permit the passage of air and moisture vapor out of the sanitary napkin 10 while blocking the passage of body fluids. A good material is a micro-embossed, polymeric film, such as polyethylene or polypropylene, having a thickness of about 0.025 to 0.13 millimeters. Bicomponent films can also be used as well as woven and nonwoven fabrics which have been treated to render them liquid-impermeable. Another suitable material is a closed cell polyolefin foam. A closed cell polyethylene foam having a thickness ranging from about 0.5 millimeters to about 10 millimeters works well.

In a preferred embodiment of the sanitary napkin 10, the cover 12 and the baffle 14 extend beyond the absorbent 16 and are bonded together to form a peripheral seal 24. The peripheral seal 24 encloses the absorbent constituents of the sanitary napkin 10 to prevent fluid leakage from the side of the absorbent 16 and to form a soft and comfortable side edge for the wearer. The cover 12 and baffle 14 can be bonded together using any means commonly known in the art for this purpose, such as by gluing, crimping, pressure and/or heat-sealing and ultrasonics.

The transfer layer 18 at least partially overlies and is in liquid communication with the absorbent 16. It is understood by those skilled in the art that the "transfer layer" may be also known as an intake distribution layer. As used herein, these terms may be used interchangebly. Desirably, the transfer layer 18 is positioned between the cover 12 and the absorbent 16. The transfer layer 18 can be dimensioned to have a width and length ranging from a few millimeters to the dimension of the absorbent 16. Desirably, the transfer layer 18 will have a width of about 10 millimeters to about 75 millimeters and a length less than that of the absorbent 16. To achieve the functionality of absorbing both the fluid-like and the viscous components of menses, it is critical to the invention that the transfer layer 18 be substantially composed of a material having a mean free path within the range of 50 microns to about 200 microns. Preferably, the transfer layer 18 is composed of a cellulosic material. Desirably, the transfer layer 18 will have a mean free path ranging from about 50 microns to about 150 microns, and preferably, it will range from about 50 microns to about 100 microns. The "mean free path" is defined to be the average edge-to-edge, uninterrupted distance between all possible pairs of structural elements, i.e. fibers, in the matrix. The procedure for determining this parameter is described in greater detail below.

In addition to the mean free path, the transfer layer 18 preferably may have one or more of the following: an effective average pore size ranging from about 18 microns to about 60 microns and an absorbency rate of less than about 20 seconds.

Desirably, the average pore size of the transfer layer 18 will range from about 20 microns to about 60 microns and more preferably, is from about 30 microns to about 60 microns. The average pore size of the transfer layer 18 was determined using a Coulter porometer available from Coulter Electronics Ltd., Northwell Drive, Luton Beds LU33RH, England. The procedure used is described in the Operator's Manual, the disclosure of which is incorporated herein by reference.

Desirably, the absorbency rate of the transfer layer 18 is less than 15 seconds and preferably, it is less than about 10 seconds. The absorbency rate of the transfer layer 18 was determined by the following method. A sheet of poly (about 30.5 cm×15.3 cm) was placed on the lab bench to prevent blood from leaking through the absorbent. A base material (a 15.3 cm long×6.4 cm wide×1.3 cm thick fluff pulp pledget having a basis weight of 768 grams per square meter (gsm) or a 19.1 cm long×6.4 cm wide×0.6 cm thick 75% fluff/25% meltblown coform material having a basis weight of 540 gsm (3 layers of 180 gsm) with 14.3 gsm SB carrier sheet) was placed on the piece of poly. A 136 mm long×36 mm wide strip of transfer material was centered on top of base material. An acrylic block, having dimensions of 10.2 cm wide×10.2 cm long×2.5 cm thick and having a 5.1 cm long×1.3 cm wide oval hole cut out in the center with a weight of 273 grams, was placed on top and in the center of the transfer material. With the transfer material strip laying flat, 10 cc's of bovine blood, oxalate, available from Cocalico Biologicals Inc, P.O. Box 265 Reamstown, Pa. 17576, was drawn into a 20 cc syringe, (Pharmaseal 20 cc Lock Tip). Any excess blood was wiped off the syringe. The blood was then dispensed into the center of the oval hole over a time period of 3 seconds. A timer was started immediately after the blood was completely dispensed. The timer was stopped when all of the blood was observed to have been absorbed out of the acrylic block opening. The time necessary to absorb the 10 cc's of bovine blood is the absorbency rate. The acrylic block is cleaned between tests.

An example of a suitable cellulosic material that may be used as a transfer layer is an uncreped through air dried sheet (UCTAD) having a basis weight of about 30 gsm to about 120 gsm. The UCTAD sheet can be prepared by the process disclosed in U.S. Pat. No. 5,048,589 issued to Crook et al. on Sep. 17, 1991 and U.S. Pat. No. 5,399,412 issued to Sudall et al. on Mar. 21, 1995; each being commonly assigned to Kimberly-Clark Corporation. The entire disclosure of each patent is incorporated herein and made a part hereof. Broadly, the process includes the steps of forming a furnish of cellulosic fibers, water, and a chemical wet strength resin; depositing the furnish on a traveling foraminous belt thereby forming a fibrous web on top of the traveling belt; subjecting the fibrous web to noncompressive drying to remove water from the fibrous web and removing the dried fibrous web from the traveling foraminous belt.

EXAMPLE

Test specimens of polymeric transfer layers were prepared for comparison with a transfer layer of the invention. The mean free path, pore size and absorbency rate of each transfer layer specimen were evaluated, the results are in the table below. The pore size and absorbency rate were determined in accordance with the procedures described above. The mean free path was determined by computer-assisted image analysis of microtomed plastic sections of the webs, imaged by polarized light optical microscopy. Thin optical sections provide a 2-dimensional field suitable for analysis. The field is comprised of void space and fiber intercepts, from which the mean free path was derived.

Each transfer layer material was infiltrated in silicone molds with low-viscosity epoxy resin available from Ladd Research Industries, Ltd., Burlington, Vt. The resin was polymerized for 36 hours at 65° C. Ten micrometer thick sections were cut from each block using a steel knife microtome, coverslipped on a glass slide then examined using polarized light optical microscopy. Six randomly selected image fields of each material section were digitized from the microscope using a Dage MTI VE1000 CCD monochrome camera, and analyzed using a Sun Sparc20 workstation running PGT IMIX Feature Analysis software, available from Princeton Gamma Tech, Inc., 1200 State Rd., Princeton N.J. Imaging magnification was 10× for sections of higher bulk materials such as UCTAD, the bicomponent fiber materials available from Kimberly-Clark Corporation under the tradenames of "PRISM" and "TABBI" and a fibrous blend of polyester, rayon, and polymeric fiber such as that marketed by C. Itoh & Co. under the tradename "CHISSO". Imaging magnification was 25× for the denser meltblown and pulp tissue materials. Image calibration was performed at both magnifications using a certified stage micrometer (Graticules Ltd., Part #S8 McCrone Associates), divided into 10 micrometer increments. The polarized light images were binarized and processed to fill holes or voids inclusions in the fibers. The mean free path is calculated by first measuring the fraction of the total field occupied by void space. This fraction is divided by the quotient of the number of intercepts of the fibers with raster test lines in the field, divided by total unit length of all the test lines.

| Material | Basis Wt. (gsm) | MFP (μm) | MPS (μm) | Absorbency Rate Over Pulp | Absorbency Rate Over Coform |
|---|---|---|---|---|---|
| UCTAD | 60 | 75.9 | 29.6 | 12 | 5 |
| Tissue | 30 | 37.7 | 21.1 | 30 | 22 |
| Meltblown | 60 | 69.7 | 15.0 | 15 | 10 |
| [1]PRISM | 40 | 275.0 | 117.5 | 4 | 3 |
| [2]TABBI | 50 | 1584.3 | >300* | 1 | 2 |
| CHISSO | 90 | 714.1 | 81.82 | 3 | 3 |

[1]A bicomponent spunbonded fiber of polyethylene and polyproplyene described in U.S. Pat. No. 5,382,400 issued to Pike et al. on January 17, 1995, the disclosure of which is incorporated herein by reference.
[2]A bicomponent through air bonded carded web of a staple sheath fibers of polyethylene and polyester generally described in U.S. Pat. No. 3,589,956 issued to Kranz et al. on September 22, 1967, the disclosure of which is incorporated herein by reference.
*The mean pore size was greater than the ability of the apparatus to measure.

From the data set forth in the table above, it is evident that a cellulosic transfer layer having a mean free pore size ranging from about 50 microns to about 200 microns has superior wicking and absorbency compared to polymeric materials typically used in absorbent articles.

While the invention has been described with reference to a preferred embodiment and illustrated with regard to a range of optional features, those skilled in the art will appreciate that various substitutions, omissions, changes and modifications may be made without departing from the spirit hereof. Accordingly, it is intended that the foregoing description be deemed merely exemplary of the preferred scope of the present invention and not be deemed a limitation thereof.

We claim:

1. An absorbent article comprising an absorbent having a bodyfacing surface, and a transfer layer superposed over at least a portion of the bodyfacing surface and in liquid communication with said absorbent, said transfer layer comprising structural elements defining a mean free path within the range of 50 microns to about 200 microns, the mean free path being defined as an average of edge-to-edge uninterrupted distances between all pairs of said structural elements and the mean free oath being determined by dividing a void space fraction within a field by a quotient of a number of fiber intercepts with test lines in the field, divided by total unit length of all the test lines in the field.

2. The absorbent article of claim 1 wherein said transfer layer has a mean free path within the range of 50 microns to about 150 microns.

3. The absorbent article of claim 1 wherein said transfer layer has a mean free path within the range of 50 microns to about 100 microns.

4. The absorbent article of claim 1 wherein said transfer layer has a mean pore size ranging from about 18 microns to about 60 microns.

5. The absorbent article of claim 1 wherein said transfer layer has a mean pore size ranging from about 20 microns to about 60 microns.

6. The absorbent article of claim 1 wherein said transfer layer has a mean pore size ranging from about 30 microns to about 60 microns.

7. The absorbent article of claim 1 wherein said transfer layer has a bovine blood absorbency rate of less than about 20 seconds.

8. The absorbent article of claim 1 wherein said transfer layer has a bovine blood absorbency rate of less than about 10 seconds.

9. The absorbent article of claim 1 wherein said transfer layer substantially comprises a cellulosic material.

10. An absorbent article comprising:
   a. a liquid-permeable cover;
   b. an absorbent; and
   c. a cellulosic transfer layer positioned between said cover and said absorbent and which is in liquid communication with said absorbent, said transfer layer comprising structural elements defining a mean free path within the range of 50 microns to about 200 microns and a mean pore size ranging from about 18 microns to about 60 microns, the mean free path being defined as an average of edge-to-edge, uninterrupted distances between all pairs of said structural elements and the mean free path being determined by dividing a void space fraction within a field by a quotient of a number of fiber intercepts with test lines in the field, divided by total unit length of all the test lines in the field.

11. The absorbent article of claim 10 wherein said transfer layer has a mean free path within the range of 50 microns to about 150 microns.

12. The absorbent article of claim 10 wherein said transfer layer has a mean pore size ranging from about 20 microns to about 60 microns.

13. The absorbent article of claim 10 wherein said transfer layer has a bovine blood absorbency rate of less than about 20 seconds.

14. The absorbent article of claim 10 wherein said transfer layer has a mean free path within the range of 50 microns to about 150 microns.

15. A sanitary napkin comprising:
   a. a liquid-permeable cover;
   b. a liquid-impermeable baffle;
   c. an absorbent between said cover and said baffle; and
   d. a cellulosic transfer layer positioned between said cover and said absorbent and which is in liquid communication with said absorbent, said transfer layer structural elements defining a mean free path within the range of 50 microns to about 200 microns and a mean pore size ranging from about 18 microns to about 60 microns, the mean free path being defined as an average of edge-to-edge, uninterrupted distances between all pairs of said structural elements and the mean free path being determined by dividing a void space fraction within a field by a quotient of a number of fiber intercepts with test lines in the field, divided by total unit length of all the test lines in the field.

16. The sanitary napkin of claim 15 wherein said transfer layer has a mean free path within the range of 50 microns to about 100 microns and a mean pore size ranging from about 18 microns to about 60 microns.

17. The sanitary napkin of claim 15 wherein said transfer layer has a mean free path within the range of 50 microns to about 100 microns and a mean pore size ranging from about 30 microns to about 60 microns.

18. The sanitary napkin of claim 15 wherein said transfer layer has a bovine blood absorbency rate of less than about 20 seconds.

19. The sanitary napkin of claim 15 wherein said transfer layer has a bovine blood absorbency rate of less than about 10 seconds.

20. A sanitary napkin comprising:
   a. a liquid-permeable cover;
   b. a liquid-impermeable baffle;
   c. an absorbent between said cover and said baffle; and
   d. a cellulosic transfer layer positioned between said cover and said absorbent, said transfer layer comprising structural elements defining a mean free path within the range of 50 microns to about 200 microns, a mean pore size ranging from about 18 microns to about 60 microns, and a bovine blood absorbency rate of less than about 20 seconds, the mean free path being defined as an average of edge-to-edge, uninterrupted distances between all pairs of said structural elements and the mean free path being determined by dividing a void space fraction within a field by a quotient of a number of fiber intercepts with test lines in the field, divided by total unit length of all the test lines in the field.

* * * * *

UNITED STATES PATENT AND TRADEMARK OFFICE
CERTIFICATE OF CORRECTION

PATENT NO. : 6,206,865 B1  
DATED : March 27, 2001  
INVENTOR(S) : Chen et al.

Page 1 of 1

It is certified that error appears in the above-identified patent and that said Letters Patent is hereby corrected as shown below:

Column 1,  
Line 56, delete "dose" and substitute -- close --.  
Line 62, delete "dose" and substitute -- close --.

Column 2,  
Line 13, after "absorbent" insert -- . --.

Column 6,  
Line 46, delete "oath" and substitute -- path --.

Signed and Sealed this

Twenty-sixth Day of March, 2002

Attest:

*Attesting Officer*

JAMES E. ROGAN  
*Director of the United States Patent and Trademark Office*